United States Patent [19]

Fisher et al.

[11] Patent Number: 4,574,125

[45] Date of Patent: Mar. 4, 1986

[54] NAPHTHO-[1,2-B]-QUINOLIZIUM DERIVATIVES AS ANTIDIARRHEAL AGENTS

[75] Inventors: Michael H. Fisher, Ringoes; Thomas M. Jacks, Westfield, both of N.J.

[73] Assignee: Merck & Co., Inc., Rahway, N.J.

[21] Appl. No.: 603,027

[22] Filed: Apr. 23, 1984

[51] Int. Cl.[4] .............................................. A61K 31/44
[52] U.S. Cl. ................................... 514/284; 514/867; 546/73
[58] Field of Search ................... 546/73; 514/284, 867

[56] References Cited

U.S. PATENT DOCUMENTS 4,042,592  8/1977  Sawa ..................................... 546/73

Primary Examiner—Frederick E. Waddell
Attorney, Agent, or Firm—David L. Rose; Michael C. Sudol, Jr.; Mario A. Monaco

[57] ABSTRACT

There are disclosed certain naphtho-[1,2-b]-quinolizium compounds which have antidiarrheal activity. The compounds reduce fluid accumulation caused by enterotoxins produced by bacteria such as *Vibrio cholerae* or *Escherichia coli.*

7 Claims, No Drawings

NAPHTHO-[1,2-B]-QUINOLIZIUM DERIVATIVES AS ANTIDIARRHEAL AGENTS

BACKGROUND OF THE INVENTION

Certain forms of diarrhea, namely those caused by the production of enterotoxins by certain bacteria are often difficult to treat and can be life threatening. The use of normal antidiarrheal agents which merely are absorbents, such as kaolin, or agents that reduce intestinal muscle activity have little or no effect on this enterotoxin-caused diarrhea.

Cholera is an acute infection in man involving the entire small bowel, characterized by a debilitating diarrhea. Enterotoxigenic *Escherichia coli* are a major cause of diarrhea in neonatal food-producing animals and "travelers diarrhea" in man.

These enteric bacteria release enterotoxins that interact with the epithelium of the small intestine, the effects of which result in water and electrolyte transport reversing from absorption to secretion. *V. cholerae* enterotoxin and *Escherichia coli* LT enterotoxin stimulate adenylate cyclase causing increased formation of cAMP which, through a cascade of reactions, inhibits active absorption and stimulates active secretion of water and electrolytes (sodium, chloride, bicarbonate). In contrast to these two enterotoxins, *Escherichia coli* ST enterotoxin stimulates guanylate cyclase, increasing cGMP levels, which causes diarrhea primarily by inhibiting active absorption of water and electrolytes.

SUMMARY OF THE INVENTION

The instant invention provides for naphtho-[1,2-b]-quinolizium compounds as agents for the treatment of enterotoxin-caused diarrhea. Thus, it is an object of the instant invention to describe such naphtho-[1,2-b]-quinolozium compounds. An additional object is to describe processes for the preparation of such compounds. A still further object is to describe the use of such compounds in the treatment of enterotoxin-caused diarrhea and compositions for such use. Further objects will become apparent from a reading of the following description.

DESCRIPTION OF THE INVENTION

The naphtho-[1,2-b]-quinolizium compounds of this invention which have activity against enterotoxin-caused diarrhea have the following structural formula:

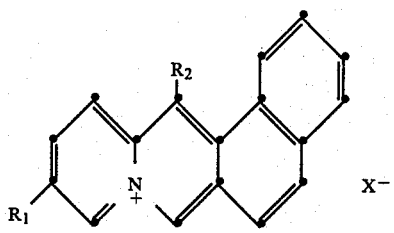

I wherein:
$R_1$ and $R_2$ are independently hydrogen, loweralkyl, loweralkoxy or halogen; and
X is halogen.

Preferred compounds of this invention are those wherein $R_1$ and $R_2$ are independently hydrogen or loweralkyl; and X is chlorine. The most preferred compound is when $R_1$ and $R_2$ are methyl.

When used in the instant application the term "loweralkyl" is intended to include those alkyl groups containing from 1–5 carbon atoms, such as, methyl, ethyl, propyl, isopropyl, butyl, sec-butyl, pentyl, and the like.

In the instant application the term "loweralkoxy" is intended to include those alkoxy groups containing from 1–5 carbon atoms, such as, methoxy, ethoxy, propoxy, isopropoxy, butoxy, isobutoxy, sec-pentoxy, and the like.

When used in the instant application the term "halogne" is intended to include the halogen atoms fluorine, chlorine, bromine and iodine.

The compounds of the instant invention are prepared according to the following reaction scheme:

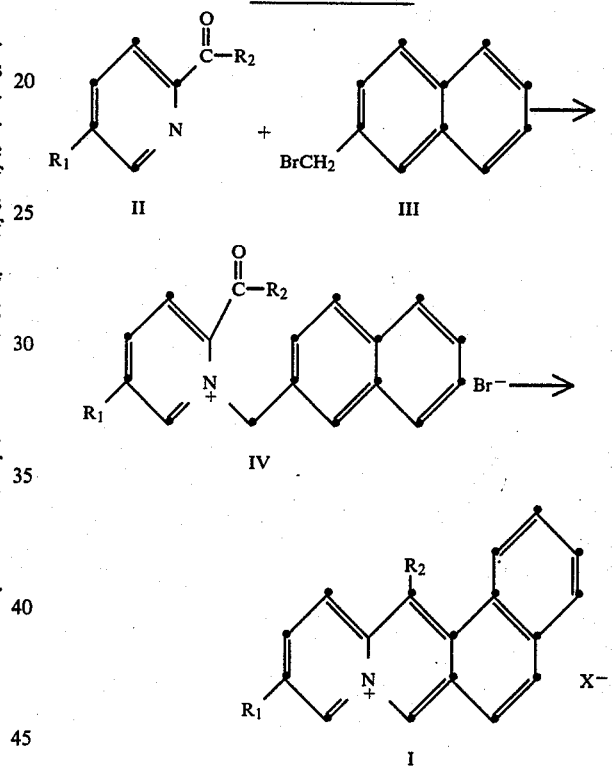

Reaction Scheme

In the first step of the reaction a 2-$R_2$ carbonyl-5-$R_1$ substituted pyridine (II) is combined with 2-bromomethylnaphthylene (III) to form compound (IV). The reaction takes place in a inert solvent such as tetramethylenesulfone, dimethylsulfoxide, N,N-dimethylformamide and the like. The reaction is heated to from 50° C. to reflux temperature, preferably about 100° C. for from ½ to 4 hours, then allowed to stand at room temperature for from 1–30 days. The product is isolated using known techniques.

Compound (III) is then treated with liquid hydrogen fluoride to cyclize the compound to the desired product. The liquid hydrogen fluoride is allowed to evaporate at room temperature and the residue is treated with an alcoholic solution of HX to prepare the desired anionic portion of the molecule. The product is isolated using techniques known to those skilled in the art.

Diarrhea induced by the enterotoxins of *Vibrio cholerea* and *Escherichia coli* released in infections of the small bowel can be serious life-threatening conditions. These enterotoxins interact with the epithilium of the bowel resulting in fluid and electrolyte loss with consequent dehydration and circulatory collapse. In severe cases of cholera in man, if untreated, the fatality rate can exceed 50 percent. *E. coli* produces a similar debilitating diarrhea in newborn animals which, if untreated, will cause a substantial number of fatalities.

The instant compounds are used to treat such cases of enterotoxin-caused diarrhea in humans and animals and may be administered in solid or liquid dosage forms either orally, parenterally or intravenously.

The Formula I compounds can be administered to patients (both human and animal) having such enterotoxin-caused diarrhea by formulating them in a composition such as tablet, capsule or elixir for oral administration: sterile solutions or suspensions can be used for parenteral administration. About 10 to 1000 mg of a compound of Formula I is compounded with a pharmaceutically acceptable vehicle, carrier, excipient, binder, preservative, stabilizer, flavor, etc., in a unit dosage form as called for by accepted pharmaceutical practice. The amount of active substance in a composition is such that dosage in the range indicated is obtained. Total daily dose administered to patients having such enterotoxin-caused diarrhea will be in the 10 to 100 mg/kg range with a preferred daily dose being 20 to 30 mg/kg of active ingredient administered either as a single dose or in multiple divided doses throughout the day. It will be realized by those skilled in the art, the dosage range for any particular patient (animal or human) will depend upon the severity of the disease treated, weight of the patient and any other conditions which the physician or other person skilled in the art will take account of.

Illustrative of the adjuvants which we have incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose, or saccharin; a flavoring agent such as peppermint, oil of wintergreen or cherry. When a dosage unit form is a capsule, it may contain, in addition to materials of the above type, a liquid carrier such as a fatty oil. Various other materials may be present as coatings or to otherwise enhance the pharmaceutical elegance of the preparation. For instance, tablets may be coated with shellac, sugar or the like. A syrup or elixir may contain the active compound, sucrose as a sweetening agent, methyl- and propylparabens as preservatives, a dye, and a flavoring such as cherry or orange flavor.

Sterile compositions for injection can be formulated according to conventional pharmaceutical practice by dissolving or suspending the active substance in a conventional vehicle such as water for injection, a naturally occurring vegetable oil like sesame oil, cocount oil, peanut oil, cottonseed oil, etc., or a synthetic fatty vehicle like ethyloleates or the like. Buffers, preservatives, antioxidants and the like can be incorporated as required.

The following examples are provided in order that the instant invention might be more fully understood. They should not be deemed limitative of the invention.

EXAMPLE 1

2-Bromo-5-methylpyridine

Five hundred grams of 2-amino-5-methylpyridine (4.81 m) was dissolved in 4300 ml of precooled (5° C., crushed ice-ethanol) 48% hydrobromic acid in a 22 liter round bottom flask fitted with a stirrer, an immersion thermometer and 1 liter dropping funnel. The temperature of the mixture rose to 15° during the amine addition and upon cooling to −5° C., 774 ml (2400 g, 30.0 m) of bromine was added while holding the temperature at 0°. The reaction became quite thick during the bromine addition, but became thinner by the end of the addition. The mixture was cooled once again to −5° C. and 845 g (12.4 mole) of sodium nitrite in 1300 ml of water was added dropwise over a period of two hours at 0°–5° C. The mixture was stirred at −5°–0° C. for one hour and then neutralized by the addition of 2.2 Kg of sodium hydroxide in 2.2 liters of water not allowing the temperature to rise over 20° C. The aqueous-oily layer which formed was then extracted with 4 liters of ether and the ether layer was washed with a solution of 450 g of sodium bisulfite in 4 liters of water (much gas evolution was observed), 2×2 liter portions of saturated sodium carbonate solution, and 2×2 liter portions of water. Concentration of the dried (anhydrous magnesium sulfate, overnight) ether layer gave 748 g of crude product which solidified on standing. This material was then dissolved in 1125 ml of hexane, filtered and cooled in ice. Tan solid crystallized and filtration gave 522 g, m.p. 42°–44° C. (Lit. m.p. 43°–45° C.). Another 108 g, m.p. 42°–44° C., was isolated by reworking the mother liquors to give a total of 630 g (76%).

2-Cyano-5-methylpyridine

Sixty grams (0.35 m) of 2-bromo-5-methylpyridine and 27 g (0.30 m) of cuprous cyanide were blended and added to a 250 ml round bottom flask fitted with an immersion thermometer, magnetic stirrer and distillation connecting head. To this head was connected an adapter attached to a 3-neck 250 ml round bottom flask containing a vacuum adapter. The mixture was warmed slowly with a yellow Bunsen flame and when the internal temperature reached 125° C. a vigorous exothermic reaction occurred. The external heat was removed and the temperature rose to over 250° C. in less than one minute. Material distilled up the side of the flask during the next two minutes with the temperature remaining above 250° C. After another two minutes the reaction subsided and the vacuum pump was started. Quite a bit of product distilled (0.30–0.50 mm) during the first few minutes without the aid of external heating. The collecting flask was cooled in crushed-ice/ethanol during this period. More product was distilled employing a Bunsen flame and a total of 31 g of product was collected. This material was dissolved in 250 ml of ether and the organic layer was washed with 2×100 ml portions of 5% aqueous sodium hydroxide and 2×100 ml portions of water and dried over anhydrous magnesium sulfate. Concentration of the ether gave 29.5 g of product which was dissolved in 300 ml of hot n-hexane. On cooling to the point of haziness (oiling out) the solution was seeded. White needle-like crystals formed almost immediately. Filtration led to the isolation of 24.5 g (59%) of product, m.p. 71°–75° C. (Lit. m.p. 72°–74° ). By reworking the mother liquor another 0.60 g, m.p. 67°–72° C. of product and 3.0 g of oil, presumably a mixture of starting material and product was isolated.

2-Acetyl-5-methylpyridine

Methylmagnesium iodide was synthesized by the addition of 142 g (1.0 m) of methyl iodide 24 g (1.0 mole) of magnesium metal in dry ether in a 3 liter round bottom flask fitted with a stirrer, dropping funnel and reflux condenser with a drying tube.

The Grignard reagent was then added dropwise at 5°-10° C. to a precooled (0°, ice-ethanol) solution of 47.2 g (0.4 m) of 2-cyano-5-methylpyridine in 500 ml of ether and 600 ml of benzene in a 5 liter round bottom flask fitted with a stirrer, drying tube, dropping funnel and immersion thermometer. After stirring at room temperature for seventy-five minutes, a cooled solution of 50 g of ammonium chloride in 300 ml of water was added to decompose the complex. Substantial foaming occurred. The organic layer was decanted and about 3 liters of water was added to the heterogenous aqueous layer. The aqueous layer was then extracted with 2×500 ml portions of ether. All organic layers were combined, washed with 2×500 ml portions of water and dried over anhydrous magnesium sulfate. Concentration gave 48.5 g of a yellow oil which was distilled to give 28.3 g of product b.p. 66°-67° C./1.7-1.8 mm (Lit. b.p. 92°-95°/15 mm).

2-Bromomethylnaphthalene

A mixture of 250 g (1.75 m) of 2-methylnaphthalene and 312.5 g (1.75 m) of N-bromosuccinimide in 1125 ml of carbon tetrachloride in a 3 liter round bottom flask fitted with a stirrer and reflux condenser with a drying tube was refluxed for twenty hours. The insoluble succinimide (171 g, 1.73 moles) was filtered and washed with 250 ml of carbon tetrachloride. Concentrated in vacuo gave 395 g of an oil to which was added 800 ml of petroleum ether. Solid crystallized immediately and was filtered and washed with 500 ml of petroleum ether. The first crop was air-dried to give 298 g, m.p. 48°-65° C. (Lit. m.p. 56°). Concentration of the filtrate led to the isolation of another 33 g, m.p. 45°-50° C. of product to give a total of 331 g (86%) of good quality crude product.

One hundred and fifty grams of this material was distilled, b.p. 126°-128°/1.000 mm (Lit. 172°-173° C./20 mm) to give 113 g (64%) of product which solidified immediately, m.p. 52°-71° C.

1-(2-Naphthylmethyl)-2-acetyl-5-methylpyridinium bromide

Twenty-six grams (0.192 m) of 2-acetyl-5-methylpyridine and 40 g (0.181 m) of 2-bromomethylnaphthalene was added to 78 ml of tetramethylene-sulfone. After heating the mixture for two hours on a steam bath, the mixture was allowed to stand at room temperature for twenty days. The reaction mixture was diluted with 700 ml of ethyl acetate and product oiled out. This first portion of ethyl acetate was decanted and the gum was extracted with 3×100 ml portions of ether. A total of 58 g (85-90%) of gum remained and after storing in the cold for one week some solid formed; however no attempt was made to purify this material further.

10,13-Dimethylnaphtho-[1,2-b]-quinolizinium chloride

Forty-eight grams of crude pyridinium bromide was added to a 2 liter polyethylene bottle containing a magnetic stirring bar and 750 ml of liquid hydrogen fluoride was collected. Two days were required for the complete evaporation of the hydrogen fluoride and the 48 g of residue was dissolved in 100 ml of alcoholic hydrochloric acid (methanol:concentrated hydrochloric acid (3:1)). This material was passed over 500 g of Amberlite IRA 410 resin (heated in boiling methanol for forty-five minutes and air-dried overnight) on the chloride cycle. Five hundred milliliters of solvent was required to remove the bulk of the product. Concentration of the solution to dryness gave 35 g of crude product. It was redissolved in 75 ml of 2BA ethanol with warming and on cooling, 75 ml of ether was added slowly. Product crystallized and was filtered, washed with 50 ml of ether, and air-dried to give 18.6 g of product m.p. 324°-326° C. (Lit. m.p. 318°-320°). The filtrate was reworked to give another 3.4 g of good quality product. Darco KB treatment and another reprecipitation from 170 ml of 2BA ethanol and 170 ml of ether gave 20.1 g of product, m.p. 324°-326° C. which; however, did not give a good elemental analysis. Pure product was finally isolated by recrystallization from 55 ml of hot 2BA ethanol. The filtrate was cooled to 5° C. and 13 g m.p. 324°-326° C. of first crop material was collected. Another 4.3 g of product, m.p. 324°-326° C., was isolated by reworking the mother liquor to give a total of 17.3 g (43%), K.F. for ($H_2O$)=4.0%. (All melting points taken in an oil bath preheated to 310° C.)

Physical and Analytical Data

Anal. Analytical sample pig dried at 100° in vacuo. Calcd. for $C_{19}H_{16}NCl$ (293.80): C, 77.67; H, 5.49; N, 4.76; Cl, 12.07. Found: C, 77.55; H, 5.74; N, 5.02; Cl, 11.97.

Spectral Data

Infrared Consistent with the proposed structure.

| Ultraviolet | | |
|---|---|---|
| 95% EtOH | | |
| max (mμ) | 407.5 | (= 11,225) |
| | 385.0 | (= 11,840) |
| | 370.0 | (= 9,578) |
| | 323.0 | (= 35,475) |
| inf. | 313.0 | (= 25,500) |
| inf. | 301 | (= 16,275) |
| | 277.7 | (= 40,600) |
| shd. | 272.5 | (= 37,340) |
| | 233 | (= 23,070) |
| | 218 | (= 20,330) |
| Approximate Solubilities - at room temperature | | |
| $H_2O$ | | = 1 g sol. in 44 ml |
| DMF/$H_2O$(1:1) | | = 1 g sol. in 24 ml |
| DMA/$H_2O$(1:1) | | = 1 g sol. in 46 ml |
| Propylene glycol | | = 1 g sol. in 10 ml |

EXAMPLE 2

The compound 10,13-dimethylnaphtho-(1,2-b)-quinolizium chloride has been shown to reduce the intestinal secretory response (diarrhea) due to sterile cholera and *Escherichia coli* enterotoxins. In mice the compound reduced the secretory response due to *Escherichia coli* ST by 81% compared to a 77% reduction by berberine. In rabbits, a 46% reduction in the secretory response due to cholera enterotoxin was achieved with 10,13-dimethylnaphtho-(1,2-b)-quinolizium chloride. Berberine, a known antidiarrhea agent, achieved a comparable result.

What is claimed is:

1. A method for the treatment of enterotoxin-caused diarrhea which comprises administering to a human or animal afflicted with such diarrhea an effective amount of a compound having the formula:

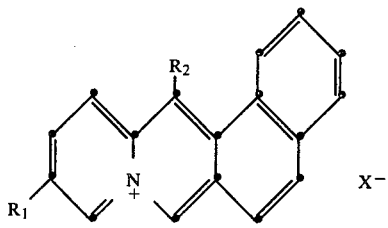

wherein:

R₁ and R₂ are independently hydrogen, loweralkyl, loweralkoxy or halogen; and

X is halogen.

2. The method of claim 1 wherein the enterotoxin caused diarrhea is caused by *Vibrio cholerae* or *Escherichia coli*.

3. The method of claim 2 wherein the compound administered has R₁ and R₂ independently hydrogen or loweralkyl; and X is chlorine.

4. The method of claim 3 wherein the compound administered has R₁ and R₂ as methyl.

5. A composition useful for the treatment of enterotoxin-caused diarrhea which comprises an inert carrier and a compound of claim 1.

6. A composition of claim 9 wherein the compound has R₁ and R₂ independently hydrogen or loweralkyl; and X is chlorine.

7. The composition of claim 10 wherein the compound has R₁ and R₂ as methyl.

* * * * *